（12）United States Patent
Lewensohn et al.

US006992207B2

(10) Patent No.: US 6,992,207 B2
(45) Date of Patent: Jan. 31, 2006

(54) MELPHALAN DERIVATIVES AND THEIR USE AS CANCER CHEMOTHERAPEUTIC DRUGS

(75) Inventors: Rolf Lewensohn, Danderyd (SE); Joakim Gullbo, Uppsala (SE); Rolf Larsson, Uppsala (SE); Hans Ehrsson, Bromma (SE); Kristina Luthman, Gothenburg (SE)

(73) Assignee: Oncopeptides AB, Danderyd (SE)

( * ) Notice: Subject to any disclaimer, the term of this patent is extended or adjusted under 35 U.S.C. 154(b) by 379 days.

(21) Appl. No.: 10/297,588

(22) PCT Filed: Jun. 11, 2001

(86) PCT No.: PCT/SE01/01318

§ 371 (c)(1),
(2), (4) Date: Dec. 13, 2002

(87) PCT Pub. No.: WO01/96367

PCT Pub. Date: Dec. 20, 2001

(65) Prior Publication Data

US 2004/0097421 A1 May 20, 2004

Related U.S. Application Data

(60) Provisional application No. 60/211,227, filed on Jun. 13, 2000.

(30) Foreign Application Priority Data

Jun. 13, 2000 (SE) .................................. 0002202

(51) Int. Cl.
C07C 229/00 (2006.01)
C07C 233/00 (2006.01)
C07C 241/00 (2006.01)
A61K 38/00 (2006.01)

(52) U.S. Cl. ........................ 560/41; 562/450; 564/123; 564/149; 564/152; 564/155; 564/157; 514/2

(58) Field of Classification Search .................. 560/41; 562/450; 564/123, 149, 152, 155, 157; 514/2
See application file for complete search history.

(56) References Cited

U.S. PATENT DOCUMENTS

| | | | |
|---|---|---|---|
| 3,032,584 A | * | 5/1962 | Stock et al. ................ 562/449 |
| 4,216,208 A | * | 8/1980 | DeBarbieri et al. ......... 424/177 |
| 4,314,999 A | * | 2/1982 | DeBarbieri et al. ......... 424/177 |
| 4,428,875 A | * | 1/1984 | DeBarbieri et al. ... 260/112.5 R |
| 4,540,683 A | * | 9/1985 | DeBarbieri et al. ........... 514/18 |
| 4,740,501 A | * | 4/1988 | DeBarieri et al. ............ 514/18 |

OTHER PUBLICATIONS

Tsay et al. Phase I study of beta-alanyl-melphalan as a potent anticancer drug. □□Cancer, Chemotherapy and Pharmacology, 1987, vol. 19 (3) p 190-196.*

Medzihradszky-Schweiger et al. A Melphalan Containing Cyclic Melantropin Analog with Prolonged Biological Activity. Peptides, 1996, p631-632.*

Yagi et al. Increased cancericidal activity of PTT.119, a new synthetic bis-(2-chloroethyl)amino-L-phenylalanine derivative with carrier amino acids. Cancer, Chemoth rapy and Pharmacology, 1984, vol. 12 (2), p 70-76.*

STN International, file CAPLUS, CAPLUS accession No. 1967:27517, document No. 66:27517 I.N. Romanova et al.: "Effect of salin and sarcolysine on oxidative phosphorylation in mitochondria from tumor and normal cells" Vopr. Med. Khim., vol. 12, No. 6, pp. 586-591, 1966.

STN International, file CAPLUS, CAPLUS accession No. 1973:500709, document No. 79:100709 P.V. Lopatin et al.: "Antineoplastic activity of some N-acetylsarcolysine derivatives in the form of nonaquenous solutions" Farmakol. Toksikol., vol. 36, No. 4, pp. 479-480 1973.

Lidia Kupczyk et al.: "Derivatives of melphalan designed to enhance drug accumulation in cancer cells" Journal of Drug Targeting, vol. 4, No. 6, pp. 359-370 1997.

* cited by examiner

*Primary Examiner*—Samuel Barts
*Assistant Examiner*—Sikarl A. Witherspoon
(74) *Attorney, Agent, or Firm*—Oblon, Spivak, McClelland, Maier & Neustadt, P.C.

(57) ABSTRACT

The invention refers to new alkylating di- and tripeptides based on a melphalan unit, and one or two additional amino acids or amino acid derivatives, which can be used in the treatment of carcinogenic diseases. Further, the invention refers to a pharmaceutical composition comprising the alkylating peptides of the invention.

17 Claims, 2 Drawing Sheets

MELPHALAN DERIVATIVES AND THEIR USE AS CANCER CHEMOTHERAPEUTIC DRUGS

The present invention relates to new melphalan derivatives useful as alkylating cancer chemotherapeutic drugs.

BACKGROUND OF THE INVENTION

Cancer is a major and often fatal disease. Accordingly, efforts to develop new therapies for cancer is a constantly ongoing effort of the research society. The vast majorities of cancers are present as solid tumours, e.g. lung cancer, breast cancer, prostate cancer, while the rest are hematological and lymphoid malignancies, e.g. leukemias and lymphomas.

Chemotherapy is used in attempts to cure or palliate the disease. In most cases this therapy is delivered in the form of combination chemotherapy, when two or more drugs having different modes of action are used together in order to optimise the antitumoural effect and to minimise side effects. The results obtained with chemotherapy vary according to tumour type. Some tumours are very sensitive and the treatment has then a high probability of leading to cure. Examples of this type of tumours are acute leukemias, malignant lymphomas, testicular cancer, chorion carcinomas and Wilms tumour. In another group of tumours chemotherapy can result in good palliation and prolonged survival. Examples of such tumours are breast cancer, colorectal cancer, ovarian cancer, small-cell lung cancer, bladder cancer, multiple myeloma, and chronic leukemias of both lymphatic and myeloid type. Primary drug resistant tumours are for instance malignant glioma, melanoma, prostate cancer, sarcomas and gastrointestinal tumours other than colorectal cancers.

Alkylating agents, such as drugs derived from nitrogen mustard, that is bis(2-chloroethyl)amine derivatives, are used as chemotherapeutic drugs in the treatment of a wide variety of neoplastic diseases. These drugs all act by covalent interaction with nucleophilic heteroatoms in DNA or proteins. It is believed that these difunctional agents are able to crosslink a DNA chain within a double helix in an intrastrand or interstrand fashion, or to crosslink between DNA and proteins. The crosslinking results in inhibitory effects on DNA replication and transcription with subsequent cell death. The drugs can be used as single agents or in combination with other antineoplastic agents. Alkylating agents seem to have some propensity for fast growing tissues. They exert effects in a broad spectrum of tumours. Side effects are mainly restricted to bone marrow and at very high doses also to the gastrointestinal tract.

Melphalan, or p-bis-(2-chloroethyl)-aminophenylalanine, is a conjugate of nitrogen mustard and the amino acid phenylalanine, which was synthesised in the mid 1950s (U.S. Pat. No. 3,032,584). This classic alkylating substance soon became a valuable drug in the chemotherapeutic field and is still of importance in the treatment of for example myeloma. Melphalan was originally developed as a selective cytotoxic agent against melanoma cells, which utilise large amounts of phenylalanine in melanin synthesis. Clinical use of melphalan in the treatment of metastatic melanomas has, however, had limited efficacy.

In the search for a more selective action on malignant cells melphalan analogues have been synthesised. Sarcolysine, m-bis-(2-chloroethyl)aminophenylalanine, was obtained by shifting the bis-(2-chloroethyl)-amino group from the para- to the meta-position of phenylalanine. By covalent conjugation of different amino acids at the amino and carboxylate groups of sarcolysine a peptide mixture known as Peptichemio® (PTC) was prepared. PTC consisted of six different peptides (de Barbieri, "Proceedings of the symposium on Peptichemio", Milan, Nov. 18, 1972). PTC was subsequently shown to be active on several tumour types as well as on tumours resistant to treatment with alkylating agents including melphalan and entered clinical trials with promising results. For the understanding of the effects and usage of PTC a serious disadvantage was the fact that it is a mixture of six peptides. The cytotoxic effects of each of the different peptides contained in PTC were therefore measured separately (Lewensohn et al., Anticancer Research 11: 321–324 (1991)) and a wide variation in the cytotoxicities of the peptides was found. One of the peptides, L-prolyl-m-L-sarcolysyl-L-p-fluorophenylalanine ethyl ester hydrochloride (P2) turned out to be more toxic to RPMI 8322 melanoma cells than any of the other peptides.

PRIOR ART

Lopatin et al. (CA 79:100709, Farmakol. Toksikol. (Moscow), 1973, 36(4), 479–480) discloses that administration of the melphalan derivatives asaley and astyron inhibited sarcoma 45 growth in rats. Astyron, or N-acetyl-L-melphalanyl-L-tyrosine ethyl ester, as well as asaley, or N-acetyl-L-melphalanyl-L-valine ethyl ester, have an acetylated amino group, which generally means that the cytotoxicity of the compound to tumour cells has been considerably reduced compared to the non acetylated form.

Romanova et al. (CA 66:27517, Vopr. Med. Khim, 1966, 12 (6), 586–91) refers to a compound called sarcolysine or salin, which according to Western nomenclature should rather be named L-melphalanyl-L-valine. This compound disrupted oxidative phosphorylation in mitochondria from rat liver homogenates and Jensen sarcoma cells.

There is a slight confusion as to the nomenclature of the melphalan derivatives. When, in 1955, a British research group reported the synthesis and cytotoxic activity of a phenylalanine derivative substituted with a bis-(2-chloroethyl)amino group in the para-position of the aromatic ring, the DL, L and D isomers were named merphalan, melphalan and medphalan, respectively. A Russian group at the same time independently named the racemic form (DL) of 4-[bis-(2-chloroethylamino)]-phenylalanine sarcolysine. Later the term sarcolysine started to be used also for the meta-phenylalanine mustard. This name confusion has continued, but today melphalan and sarcolysine are normally used for the para- and meta-derivatives, respectively.

Kupczyk-Subotkowska et al. (Journal of Drug Targeting, 1997, 4(6), 359–370) discloses derivatives of melphalan designed to enhance the accumulation of melphalan into cancer cells. A number of dipeptides comprising melphalan and valine or glutamic acid were tested and it was concluded that the cellular uptake of said dipeptides as well as of their esters probably took place via passive diffusion rather than by an amino acid or oligopeptide transporter.

One problem with the usage of bifunctional alkylating agents is primary, i.e. intrinsic, and secondary, i.e. acquired, tumour resistance to the treatment. Attempts have been made to circumvent resistance by increasing the dose of alkylating agent administered to the patient. It is, however, unclear how much this increases the effective dose at the tumour cell level.

There is an urgent need for new antitumour drugs in a wide variety of tumour diseases, especially in tumours showing primary resistance to conventional therapy, and/or in tumour diseases that have developed resistance, secondary resistance, after having responded to treatment with conventional cancer chemotherapeutics.

SUMMARY OF THE INVENTION

The object of the invention is to provide a melphalan derivative having an improved cytotoxic activity in human tumour cells.

The invention refers to dipeptides and tripeptides containing a melphalan unit, and one or two additional amino acids or amino acid derivatives, to the use of said peptides as medicaments, and to pharmaceutical compositions comprising the peptides of the invention for use as medicaments, especially for the treatment of various malignant tumours.

The melphalan derivatives of the invention exhibit an increased efficacy on a variety of tumour types. The hypothesis of the inventors is that the tumour cell uptake and intracellular accumulation of the peptides of the invention will be increased.

DESCRIPTION OF THE INVENTION

The present invention relates to new peptides of phenylalanine mustard comprising p-[bis(2-chloroethyl)amino]-L-phenylalanine mustard, L-PAM, and p-[bis(2-chloroethyl)-amino]-D-phenylalanine mustard, D-PAM, covalently linked to one or two amino acids or amino acid derivatives forming alkylating di- or tripeptides. The L-forms are, however, preferred.

The present invention refers to new melphalan derivatives, and especially to a di- or tripeptide having the formula I (I)

wherein $R_1$ is alkyloxy, cycloalkyloxy, aryloxy, arylalkyloxy, $NH_2$, alkylamino, cycloalkylamino or arylamino;
$R_2$ is (IV)

wherein $R_3$ is independently $NH_2$, OH, O-alkyl, N-alkyl, O-acyl, NH-acyl, $N(CH_2CH_2Cl)_2$, $NO_2$, F, $CF_3$ or H, and n is 1 or 2;

X is (II)

wherein $R_5$ is H;
$R_4$ is a natural or modified cyclic or aromatic amino acid, or H; as well as pharmaceutically acceptable salts thereof.

In said formulas alkyl preferably is a lower alkyl, that is alkyl having 1–4 carbon atoms.

If n in the formula I is 1, the substituent $R_3$ can be in ortho-, meta- or para-position. If n is 2, the two substituents $R_3$ can be the same or different.

Natural amino acids refers to amino acids that are normally existing and exerting their functions in living organisms. Modified amino acids refers to amino acids that in some way have been modified into a different chemical structure and chemical composition than a natural amino acid. An example of a natural cyclic amino acid is proline. Examples of aromatic amino acids are phenylalanine, tyrosine, tryptophan, and histidine.

The N-terminus of the melphalan molecule should preferably not be protected as amide or carbamate, this means that $R_4$ should preferably not be a protecting group, such as formyl, acetyl or propionyl, or benzoyl, as the protected form of the compound in general has a lower cytotoxic activity than the corresponding free form.

Pharmaceutically acceptable salts are for instance acid addition salts, such as salts of HCl, HBr, and methane sulphonic acid.

A preferred di- or tripeptide of the invention has the formula V (V)

wherein $R_1$ is alkyloxy, cycloalkyloxy, aryloxy, arylalkyloxy, $NH_2$, alkylamino, cycloalkylamino or arylamino;
$R_3$ is $NH_2$, OH, O-alkyl, N-alkyl, O-acyl, NH-acyl, $N(CH_2CH_2Cl)_2$, $NO_2$, F, $CF_3$ or H; and
$R_4$ is a natural or modified cyclic or aromatic amino acid, or H; as well as pharmaceutically acceptable salts thereof.

A specially interesting group of peptides in accordance with the invention are peptides of the formula I or V, wherein $R_3$ is F.

Dipeptides in accordance with the invention are peptides of the formula I or V, wherein $R_1$ is alkyloxy; $R_3$ is F, $CF_3$, H, OH, O-alkyl, $NO_2$, $N(CH_2CH_2Cl)_2$, NH-acyl or $NH_2$; and $R_4$ is H.

Examples of preferred dipeptides are L-melphalanyl-p-L-fluoro-phenylalanine ethyl ester (J1), L-melphalanyl-p-L-fluoro-phenylalanine isopropyl ester (JV28), and pharmaceutically acceptable salts thereof.

Tripeptides in accordance with the invention are peptides of the formula I or V, wherein $R_1$ is alkyloxy; $R_3$ is F, $CF_3$, H, OH, O-alkyl, NH-acyl, $NO_2$, $N(CH_2CH_2Cl)_2$ or $NH_2$; and $R_4$ is a natural or modified cyclic or aromatic amino acid.

An example of a preferred tripeptide is L-prolyl-L-melphanalyl-p-fluorophenylalanine ethyl ester (J3), and pharmaceutically acceptable salts thereof.

All dipeptide derivatives of the invention can be synthesised from tert.butoxycarbonyl(Boc)-protected melphalan. The coupling of Boc-melphalan to different esters or amides was performed using either (benzotriazol-1-yloxy)tripyrrolidino-phosphonium hexafluorophosphate (PyBOP)/triethylamine or 1-[3-dimethylamino)propyl]-3-ethylcarbodiimide hydrochloride (EDC)/N-methylmorpholine (NMM)/1-hydroxybenzotriazole (HOBt) as coupling reagents. Purification procedures using silica gel chromatography allowed the isolation of pure products. Removal of the Boc-group was performed in HCl saturated ethyl acetate. The dipeptide hydrochloride salts were purified by recrystallisation in ethanol/diethyl ether.

In the synthesis of tripeptide derivatives Boc-protected amino acids were coupled to the melphalan containing dipeptide derivative using EDC/NMM/HOBt as coupling reagents. Deprotection using HCl saturated ethyl acetate followed by recrystallization (EtOH/diethyl ether or EtOAc/diethyl ether) allowed the isolation of pure tripeptide hydrochloride salts.

The invention also refers to the use of a peptide as described above as a medicament, as well as for the manufacture of a medicament for treatment of malignant tumours.

The alkylating peptides of the invention were found to display a broad spectrum of activity with increased potency compared to melphalan and L-prolyl-L-sarcolysyl-p-L-fluorophenylalanine ethyl ester (P2) on tumour cell lines of different histologies and also on tumour cell lines that display L-PAM resistance. Moreover, the alkylating peptides were found to be significantly more effective compared to melphalan and P2 on freshly obtained human tumour samples of different origin, both hematological and solid, as shown in the examples given below.

The peptides of the invention may be used as first line treatment, either alone or in combination with other drugs or concomitant or sequenced with radiotherapy, of the following tumour diseases and/or stages of the respective disease:

(I) Solid tumours: for operable breast cancer as neoadjuvant or adjuvant treatment as well as for the treatment of advanced inoperable breast cancer, for small cell lung cancer of LD (Limited Disease) or ED (Extensive Disease) type, for operable stages of non-small cell lung cancer as neoadjuvant treatment, for inoperable stage III B or IV of non-small cell lung cancer, for operable (neoadjuvant) and inoperable head and neck cancer and esophageal cancer, for operable ovarian cancer as adjuvant treatment and for advanced ovarian cancer, for advanced cervical cancer, for squamous cell and basal cell carcinoma of the skin which is non-amendable to surgery or radiotherapy and for neuroblastoma. The above mentioned tumour types represent (1) tumours, which have shown sensitivity to treatment with alkylating agents, but in which this conventional therapy is not efficient enough, or (2) tumours that frequently relapse after a first remission and at that stage show less sensitivity to conventional therapy (resistance). Other groups of tumours which would be reasonable to treat with the new peptides are different stages of bladder cancer, advanced prostate cancer, malignant melanoma, colo-rectal cancer and soft tissue sarcomas where palliative results frequently have been obtained with alkylating agents. Still another group of tumours to treat are the generally drug resistant tumours like renal cancer and brain tumours.

(II) Hematological and lymphatic tumours: multiple myeloma, high and low grade lymphomas, Mb.Hodgkin, chronic lymphocytic leukemia, acute myelogenous or lymphocytic leukemia and chronic myelogenous leukemia.

Another object of the invention is a pharmaceutical composition for the treatment of malignant tumours, which comprises at least one peptide as described above together with at least one pharmaceutically acceptable carrier and/or excipient.

A pharmaceutical composition according to the invention can be used for the treatment of breast cancer, lung cancer, ovarian cancer, leukemias, lymphomas and multiple myeloma.

The pharmaceutical compositions are prepared in a manner known to a person skilled in the pharmaceutical art. The carrier or the excipient could be a solid, semi-solid or liquid material that could serve as a vehicle or medium for the active ingredient. Suitable carriers or excipients are known in the art. The pharmaceutical composition could be adapted to parenteral, oral or topical use and could be administered to the patient as tablets, capsules, solutions, suspensions, ointments or the like.

For parenteral administration the peptides according to the invention can be incorporated into a solution or suspension. Parenteral administration refers to the administration by injection, for instance by intravenous, intracapsular, intrathecal, intrapleural, intratumoral, or intraperitoneal injection or intravesically. Intravenous administration is preferred. Bone marrow may also be treated in vitro. The pharmaceutical composition should contain at least 0.001% by weight of an active peptide according to the invention, preferably 0.1–10% by weight.

The solutions or suspensions could also comprise at least one of the following adjuvants: sterile diluents such as water for injection, saline, fixed oils, polyethylene glycols, glycerol, propylene glycol or other synthetic solvents, antioxidants such as ascorbic acid or sodium bisulfite, buffers such as acetates, citrates or phosphates, and agents for adjustment of the tonicity such as sodium chloride or dextrose. The parenteral preparation could be enclosed into ampoules, disposable syringes or multiple dosage vessels made of glass or plastic.

For intravenous injection, the pharmaceutical composition of the invention may be administered by means of two vials, whereby vial I comprises the peptide as a hydrochloric salt, with and without a carrier or compound that increases solubility or effects the stability, and vial II comprises a mixture of propylenglycol/ethanol. The peptide will be dissolved immediately prior to the administration and mixed with 5% glucose or saline. The dose given might be in the range of 0.1 mg/kg–1 mg/kg given as a short infusion.

For topical administration the peptides according to the invention could be incorporated into a solution, suspension, or ointment. Said compositions could contain at least 0.1% by weight of the active peptide, preferably 0.1–10% by weight.

Another object of the invention is a method for the treatment of malignant tumours in a subject in need thereof, comprising administrating a pharmaceutically effective dose of a peptide described above. Subject refers to any mammal, preferably a human.

EXAMPLES

Syntheses of Compounds

In the following examples of synthesis of melphalan derivatives of the invention, as well as comparative compounds, all solvents were of analysis or synthesis grade. 1-Hydroxybenzotriazole, HOBt; N-methylmorpholine, NMM; and/or 1-[3-(dimethylamino) propyl]-3-ethylcarbodiimide hydrochloride, EDC; or (benzotriazol-1-yloxy)-tripyrrolidino-phosphonium hexafluorophosphate, PyBOP; and triethyl amine were used as coupling reagents. Melting points were measured in a Büchi Melting Point B-540 apparatus. $^1$H- and $^{13}$C NMR-spectra were obtained on a JEOL JNM-EX 400 NMR-spectrometer. $^1$H-spectra were recorded at 400 MHz and $^{13}$C-spectra at 100 MHz, respectively. The reactions were monitored by thin-layer chromatography (TLC), on silica plated aluminum sheets (Silica gel 60 P254, E. Merck), detecting spots by UV-light and/or 2% ninhydrin in ethanol followed by heating. Column chromatography was performed on wet packed silica (Silica gel 60 (0.040–0.063 mm), E. Merck) using flash chromatography.

The L-melphalan used as a starting compound was obtained from Sigma and was recrystallised from ethanol prior to use. The intermediate N-tert-butoxycarbonyl-L-melphalan was synthesised according to Pai, N. N.; Miyawa, J. H.; Perrin, J. H. *Drug Dev. Industr. Pharm.* 1996, 22, 181–184. L-Melphalan (500 mg, 1.64 mmol) was dissolved in 50% aqueous THF (5 ml) and triethylamine (201 µl, 1.44 mmol) was added. The solution was cooled to 0° C. and di-tert-dibutyl-dicarbonate (210 mg, 0.96 mmol) dissolved in THF (3 ml) was added dropwise. The solution was stirred for 30 min at 0° C. and then for 18 h at room temperature (RT). The solvent was evaporated off and water was added and the solution was acidified to pH 5 with 10% citric acid. After extraction three times with ethyl acetate the combined organic extract was dried over $MgSO_4$. The solvent was evaporated off and the residue was purified by flash chromatography on silica using chloroform:methanol in 3:1 and 19:1 as eluents affording 48% of a pure product. $^1$H NMR ($CDCl_3$) δ 7.05 (d, 2H, Ph-H), 6.58 (d, 2H, Ph-H), 4.98 (br s, 1 H, NH), 4.47 (br s, 1 H, α-H), 3.69–3.49 (m, 8H, 4 $CH_2$-mustard), 3.12–2.91 (m, 2H, $CH_2$-Ph), 1.40 (s, 9H, $CH_3$-Boc).

Example 1

L-Melphalanyl-L-p-fluorophenylalanine ethyl ester hydrochloride (J1)

L-p-Fluorophenylalanine (217 mg, 1.18 mmol) was dissolved in EtOH (5 ml) previously bubbled with HCl. The reaction was brought to 100° C. and was allowed to reflux for 18 hours. The solvent was evaporated off and the product was dried under high vacuum, affording L-p-fluorophenylalanine ethyl ester hydrochloride as dry white crystals (98%). $^1$H NMR: ($CD_3OD$) δ 7.30–7.26 (m, 2H, Ph-H), 7.13–7.06 (m, 2H, Ph-H), 4.29–4.22 (m, 2H, $CH_2$-Ph), 3.31–3.10 (m, 3H, $CH_2CH_3$, α-H), 1.24 (t, 3H, $CH_2CH_3$).

N-tert-Butoxycarbonyl-L-melphalan (157 mg, 0.387 mmol) was dissolved in dichloromethane (4 ml). PyBOP (201 mg, 0.387 mmol) and triethylamine (54 µl, 0.387 mmol) were added and the solution was stirred at room temperature for 1 h. A solution of L-p-fluorophenylalanine ethyl ester hydrochloride (92 mg, 0.387 mmol) and triethylamine (54 µl, 0.387 mmol) in dichloromethane (4 ml) was added and the reaction was stirred over night. The reaction was stopped by extraction with saturated $NaHCO_3$ followed by 10% citric acid. The organic layer was dried by $MgSO_4$ and the solvent evaporated to give 200 mg of a yellow oil which was purified by gradient column chromatography using ether:pentane (1:2, 1:1, 1:0) as eluent to afford 102 mg (43% yield) of N-tert-butoxycarbonyl-L-melphalanyl-L-p-fluorophenylalanine ethyl ester which was used in the next step-without further purification.

N-tert-Butoxycarbonyl-L-melphalanyl-L-p-fluorophenylalanine ethyl ester (64 mg, 0.11 mmol) was dissolved in 5 ml EtOAc previously bubbled with HCl (gas). The mixture was stirred at RT for 30 minutes. The solvent was removed in vacuo. The residue was recrystallized from $EtOH/Et_2O$. L-Melphalanyl-L-p-fluorophenylalanine ethyl ester hydrochloride (J1) was isolated as white crystals.

$^1$H NMR: ($CD_3OD$) δ 7.23 (d, 2H, Ph-H, Phe), 7.13 (d, 2H, Ph-H, Phe), 7.01 (d, 2H, Ph-H, Mel), 6.72 (d, 2H, Ph-H, Mel), 4.68 (dd, 1H, α-CH, Phe), 4.61 (br s, 1H, α-CH, Mel), 4.12 (q, 2H, $CH_2CH_3$), 3.80–3.62 (m, 8H, $CH_2$-mustard), 3.22–2.86 (m, 4H, $CH_2$-Ph), 1.21 (t, 3H, $CH_2CH_3$). Elemental analysis CHN 53.7;5.8;7.9 (calculated 54.1;6.1;7.9)

Example 2

L-Prolinyl-L-melphalanyl-L-p-fluorophenylalanine ethyl ester hydrochloride (J3)

N-tert-Butoxycarbonyl-L-proline (12 mg, 0.054 mmol), L-melphalanyl-L-p-fluorophenylalanine ethyl ester hydrochloride (24 mg, 0.045 mmol), HOBt (8 mg, 0.054 mmol), and NMM (7 µl, 0.045 mmol) were dissolved in dichloromethane (5 ml). The solution was cooled to 0° C. and EDC hydrochloride (11 mg, 0.045 mmol) was added. The solution was stirred for 1 h at 0° C. and then overnight at RT. The reaction mixture was diluted to 10 ml with dichloromethane and the reaction stopped by successive extractions with 10% aqueous citric acid, saturated $NaHCO_3$ and brine. The organic phase was dried over anhydrous $Na_2SO_4$ and the solvent evaporated off under reduced pressure to afford 27 mg (86%) N-tert-butoxycarbonyl-L-prolinyl-L-melphalanyl-L-p-fluorophenylalanine ethyl ester that was used in the next step without further purification.

$^1$H NMR ($CDCl_3$) δ 7.08–6.89 (m, 6H, Ph-H, Phe, Mel), 6.67 (br s, 1H, NH), 6.55 (d, 2H, Ph-H), 6.24 (br s, 1H, NH), 4.72 (m, 1H, α-CH), 4.55 (br s, 1H, α-CH), 4.20 (br s, 1H, α-CH), 4.10 (q, 2H, $CH_2CH_3$), 3.74–3.54 (m, 8H, $CH_2$-mustard), 3.42–3.20 (m, 2H, proline δ), 3.10–2.86 (m, 4H, $CH_2$-Ph), 2.20–1.74 (m, 4H, proline β,γ), 1.40 (s, 9H, $CH_3$-Boc), 1.18 (t, 3H, $CH_2CH_3$).

N-tert-Butoxycarbonyl-L-prolinyl-L-melphalanyl-L-p-fluorophenylalanine ethyl ester (25 mg) was dissolved in HCl saturated ethyl acetate (3 ml). The mixture was stirred at RT for 30 minutes. The solvent was removed in vacuo. Recrystallization from ethyl acetate and diethyl ether yielded pure J3 as off-white crystals in 94% yield (calculated from L-melphalanyl-L-p-fluorophenylalanine ethyl ester hydrochloride).

$^1$H NMR ($CD_3OD$) δ 7.26–6.94 (m, 6H, Ph-H, Phe, Mel), 6.68 (d, 2H, Ph-H), 6.24 (br s, 1H, NH), 4.62–4.55 (m, 2H, α-CH), 4.20–4.05 (m, 3H, α-CH, $CH_2CH_3$), 3.74–3.54 (m, 8H, $CH_2$-mustard), 3.25–2.75 (m, 6H, $CH_2$-Ph, proline δ), 2.40–1.85 (m, 4H, proline β,γ), 1.23 (t, 3H, $CH_2CH_3$).

Example 3

L-Melphalanyl-L-phenylalanine ethyl ester hydrochloride (JV22)

N-tert-Butoxycarbonyl-L-melphalan (150 mg; 0.37 mmol) was dissolved in 2.6 ml dichloromethane. PyBOP (199 mg; 0.38 mmol) and triethylamine (104 µl; 0.75 mmol) were added. After stirring at RT for 30 minutes a solution of triethylamine (104 µl; 0.75 mmol) and phenylalanine ethyl ester hydrochloride (89 mg; 0.39 mmol) in 2.6 ml dichloromethane was added. After 4 h at RT the reaction was quenched. Dichloromethane was added up to a total volume of 20 ml before extraction with 20 ml saturated aqueous NaHCO$_3$ and 20 ml 10% citric acid. The organic layer was dried (MgSO$_4$), filtered and concentrated in vacuo. The crude product was purified by column chromatography on silica using a gradient of ether:pentane (2:1→3:1), followed by ether and thereafter by CHCl$_3$:MeOH (19:1) as eluents. Collection and concentration of adequate fractions gave pure N-tert-butoxycarbonyl-L-melphalanyl-L-phenylalanine ethyl ester as a white solid (110 mg, 51%). Mp: 117–120° C.

$^1$H NMR (CDCl$_3$) δ 7.29–7.16 (m, 3H, Ph-H, Phe), 7.06–6.95 (m, 4H, Ph-H), 6.57 (d, 2H, Ph-H Mel), 6.28 (br s, 1H, NH, Phe), 4.92 (br s, 1H, NH, Mel), 4.76 (br s, 1H, α-CH, Phe); 4.26 (br s, 1H, α-CH, Mel), 4.10 (q, 2H, CH$_2$CH$_3$), 3.74–3.50 (m, 8H, CH$_2$-mustard), 3.12–2.84 (m, 4H, CH$_2$-Ph), 1.40 (s, 9H, CH$_3$-Boc), 1.18 (t, 3H, CH$_2$CH$_3$). $^{13}$C NMR (CDCl$_3$) δ 171.05 (2 C:s) (C=O amide and ester), 155.10 (C=O, Boc), 145.10 (C-4'), 135.84 (Ph), 130.75 (2 C:s), 129.39 (2 C:s), 128.54 (2 C:s) (Ph and C-3'), 127.13 (Ph), 125.07 (C-1'), 112.27 (2 C:s) (C-2'), 79.82 (C-Boc), 61.54 (CH$_2$CH$_3$), 55.51 (α-CH), 53.55 (2 C:s) (N—CH$_2$), 53.32 (α-CH), 40.51 (2 C:s) (CH$_2$—Cl), 38.13, 36.73 (CH$_2$-Ph), 28.35 (3 C:s) (CH$_3$-Boc), 14.17 (CH$_2$CH$_3$).

N-tert-Butoxycarbonyl-L-melphalanyl-L-phenylalanine ethyl ester (100 mg; 0.17 mmol) was dissolved in 6 ml HCl saturated ethyl acetate. The mixture was stirred at RT for 30 minutes. The solvent was removed in vacuo. Recrystallization from ethyl acetate and diethyl ether yielded pure JV22 (37 mg; 42%) as a slightly yellowish/brownish solid. Mp: 123–125° C.

$^1$H NMR (CDCl$_3$) δ 7.31–7.13 (m, 7H, Ph-H), 6.72 (d, 2H, Ph-H, Mel), 4.73–4.66 (m, 1H, α-CH-Phe), 4.12 (q, 2H, CH$_2$CH$_3$), 3.99–3.92 (m, 1H, α-CH, Mel), 3.77–3.64 (m, 8H, CH$_2$-mustard), 3.20–2.85 (m, 4H, CH$_2$-Ph), 1.18 (t, 3H, CH$_2$CH$_3$). $^{13}$C NMR (CDCl$_3$) δ 171.05, 168.42 (C=O in amide and ester), 145.96 (C-4'), 136.55 (Ph), 130.43 (2 C:s) (C-3'), 128.90 (2 C:s), 128.27 (2 C:s), 126.10 (Ph), 122.35 (C-1'), 112.58 (2 C:s) (C-2'), 61.23 (CH$_2$CH$_3$), 54.29, 54.25 (α-CH), 53.06 (2 C:s) (N—CH$_2$), 40.26 (2 C:s) (CH$_2$—Cl), 37.12, 36.29 (CH$_2$-Ph), 13.10 (CH$_2$CH$_3$).

Example 4

L-Melphalanyl-L-tyrosine ethyl ester hydrochloride (JV24)

N-tert-Butoxycarbonyl-L-melphalan (150 mg; 0.37 mmol) was dissolved in dichloromethane (3 ml). PyBOP (199 mg; 0.38 mmol) and triethylamine (104 µl; 0.75 mmol) were added. After stirring at RT for 30 minutes a solution of triethylamine (104 µl ; 0.75 mmol) and tyrosine ethyl ester hydrochloride (94 mg; 0.38 mmol) in 3 ml dichloromethane was added. After 100 min stirring at RT the reaction was quenched. Dichloromethane was added up to a total volume of 20 ml before extraction with 20 ml saturated aqueous NaHCO$_3$ and 20 ml 10% citric acid. The organic layer was dried (MgSO$_4$), filtered and concentrated in vacuo. The crude product was purified four times by column chromatography on silica using a gradient eluent systems of ether: pentane (2:1→4:1→1:0) followed by CHCl$_3$:MeOH (19: 1→97:3). Pure N-tert-butoxycarbonyl-L-melphalanyl-L-tyrosine ethyl ester was isolated as a colorless oil (59 mg; 27%).

$^1$H NMR (CDCl$_3$) δ 7.05–6.92 (m, 2H, Ph-H-Mel), 6.86–6.74 (m, 2H, Ph-H-Phe), 6.67 (d, 2H, Ph-H, Phe), 6.59–6.43 (m, 2H, Ph-H, Mel), 6.42–6.36 (m, 1H, NH, Phe), 5.00 (br s, 1H, NH, Mel), 4.81–4.70 (m, 1H, α-CH, Phe), 4.26 (br s, 1H, α-CH, Mel), 4.12 (q, 2H, CH$_2$CH$_3$), 3.70–3.53 (m, 8H, CH$_2$-mustard), 3.03–2.85 (m, 4H, CH$_2$-Ph), 1.39 (s, 9H, CH$_3$-Boc), 1.21 (t, 3H, CH$_2$CH$_3$). $^{13}$C NMR (CDCl$_3$) δ 171.21 (2 C:s) (C=O in amide and ester), 155.31 (2 C:s) (C=O Boc and C-4"), 144.96 (C-4'), 130.70 (2 C:s), 130.47 (2 C:s) (Ph and C-3'), 127.12 (Ph), 125.21 (C-1'), 115.52 (2 C:s) (Ph), 112.31 (2 C:s) (C-2'), 80.09 (C-Boc), 61.61 (CH$_2$CH$_3$), 55.84 (α-CH), 53.56 (2 C:s) (N—CH$_2$), 53.25 (α-CH), 40.55, 40.50 (CH$_2$—Cl), 37.32 (2 C:s) (CH$_2$-Ph), 28.36 (3 C:s) (CH$_3$-Boc), 14.22 (CH$_2$CH$_3$).

N-tert-Butoxycarbonyl-L-melphalanyl-L-tyrosine ethyl ester (48 mg; 81 µmol) was dissolved in 4 ml HCl saturated ethyl acetate. The mixture was stirred at RT for 30 minutes. The solvent was removed in vacuo. Recrystallization from ethyl acetate and diethyl ether yielded the pure JV24 (13 mg; 30%) as a slightly brownish solid. Mp: 150–154° C.

$^1$H NMR (CDCl$_3$) δ 7.16–6.86 (m, 4H, Ph-H), 6.75–6.65 (m, 4H, Ph-H), 4.68–4.59 (m, 1H, α-CH, Phe), 4.13 (q, 2H, CH$_2$CH$_3$), 4.02–3.94 (m, 1H, α-CH, Mel), 3.77–3.60 (m, 8H, CH$_2$-mustard), 3.21–2.71 (m, 4H, CH$_2$-Ph), 1.20 (t, 3H, CH$_2$CH$_3$). $^{13}$C NMR (CDCl$_3$) δ 170.94, 168.08 (C=O in amide and ester), 156.12 (C-4"), 145.68 (C-4'), 130.41 (2 C:s), 129.68(2 C:s), 127.03, (Ph and C-3'), 125.86 (C-1'), 114.98 (2 C:s) (Ph), 112.34 (2 C:s) (C-2'), 60.80 (CH$_2$CH$_3$), 54.48, 54.27 (α-CH), 53.07 (2 C:s) (N—CH$_2$), 40.19 (2 C:s) (CH$_2$—Cl), 36.32 (2 C:s) (CH$_2$-Ph), 12.64 (CH$_2$CH$_3$).

Example 5

L-Melphalanyl-L-p-methoxyphenylalanine ethyl ester hydrochloride (JV25)

N-tert-Butoxycarbonyl-L-tyrosine ethyl ester (228 mg; 0.74 mmol) was dissolved in 15 ml acetone, and K$_2$CO$_3$ (123 mg, 0.89 mmol) was added. Dimethyl sulfate (77.5 µl; 0.81 mmol) was carefully added and the solution was refluxed for 20 h. Solid K$_2$CO$_3$ was removed by filtration and the acetone was removed in vacuo. Purification by column chromatography on silica using CHCl$_3$:MeOH:heptane (4:1:5) as eluent yielded 214 mg (90%) of N-tert-butoxycarbonyl-L-p-methoxyphenylalanine ethyl ester as a clear oil. This intermediate was used in the next step without further characterization.

N-tert-Butoxycarbonyl-L-p-methoxyphenylalanine ethyl ester (165 mg; 0.51 mmol) was dissolved in CHCl$_3$ (8.5 ml) and iodotrimethylsilane (168µ; 1.22 mmol) was added. The solution was stirred for 40 min at RT. The reaction was quenched by addition of MeOH (175 µl; 4.3 mmol). The solvent and excess iodotrimethylsilane were removed in vacuo to yield 169 mg (149%) of the crude product (L-p-methoxyphenylalanine ethyl ester) as a brown-orange solid which was used in the next step without further purification.

$^1$H NMR (CD$_3$OD) δ 7.16 (d, 2H, Ph-H), 6.90 (d, 2H, Ph-H), 4.28–4.18 (m, 3H, CH$_2$CH$_3$, α-CH), 3.78 (s, 3H, OCH$_3$), 3.21–3.08 (m, 2H, CH$_2$-Ph), 1.24 (t, 3H, CH$_2$CH$_3$).

N-tert-Butoxycarbonyl-L-melphalan (150 mg; 0.37 mmol) was dissolved in 3 ml dichloromethane. PyBOP (199 mg; 0.38 mmol) and triethylamine (104 µl; 0.75 mmol) were added. After stirring at RT for 30 minutes a solution of triethylamine (104 µL; 0.75 mmol) and L-p-methoxyphenylalanine (124 mg; 0.55 mmol) in 3 ml dichloromethane was added. The solution was stirred at RT over night. Dichloromethane was added up to a total volume of 20 ml before extraction with 20 ml saturated aqueous NaHCO$_3$ and 20 ml 10% citric acid. The organic layer was dried (MgSO$_4$), filtered and concentrated in vacuo. The crude product was purified four times by flash column chromatography on silica, twice with ether:heptane (3:1),and twice with CHCl$_3$:MeOH (19:1) as eluents, to yield N-tert-butoxycarbonyl-L-melphalanyl-L-p-methoxyphenylalanine ethyl ester as a white solid (150 mg; 66%). Mp: 125–127.5° C.

$^1$H NMR (CDCl$_3$) δ 7.06 (d, 2H, Ph-H, Mel), 6.90 (d, 2H, Ph-H, Phe), 6.76 (d, 2H, Ph-H, Phe), 6.59 (d, 2H, Ph-H, Mel), 6.31 (br s, 1H, NH, Phe), 4.97 (br s, 1H, NH, Mel), 4.71 (br s, 1H, α-CH, Phe), 4.27 (br s, 1H, α-CH, Mel), 4.10 (q, 2H, CH$_2$CH$_3$), 3.75 (s, 3H, OCH$_3$), 3.69–3.56 (m, 8H, CH$_2$-mustard), 3.00–2.85 (m, 4H, CH$_2$-Ph), 1.40 (s, 9H, CH$_3$-Boc), 1.19 (t, 3H, CH$_2$CH$_3$). $^{13}$C NMR (CDCl$_3$) δ 171.11, 170.91 (C=O in amide and ester), 158.72 (C-4''), 155.30 (C=O, Boc), 145.03 (C-4'), 130.76 (2 C:s), 130.39 (2 C:s), (Ph and C-3'), 127.75 (Ph), 125.36 (C-1'); 113.96 (2 C:s) (Ph), 112.28 (2 C:s) (C-2'), 80.12 (C-Boc), 61.50 (CH$_2$CH$_3$), 55.81 (α-CH), 55.27 (OCH$_3$) 53.55 (2 C:s) (N—CH$_2$), 53.46 (α-CH), 40.52 (2 C:s) (CH$_2$—Cl), 37.33, 37.23 (CH$_2$-Ph), 28.34 (3 C:s) (CH$_3$-Boc), 14.20 (CH$_2$CH$_3$).

N-tert-Butoxycarbonyl-L-melphalanyl-L-p-methoxyphenylalanine ethyl ester (140 mg; 0.23 mmol) was dissolved in 17 ml HCl saturated ethyl acetate. The mixture was stirred at RT for 3 h. The solvent was removed in vacuo. The crude product was dissolved in ethanol followed by precipitation in diethyl ether affording JV25 (45 mg; 36%) as a white solid. Mp: 170–173° C.

$^1$H NMR (CDCl$_3$) δ 7.17–7.07 (m, 4H, Ph-H), 6.83 (d, 2H, Ph-H, Phe), 6.72 (d, 2H, Ph-H, Mel), 4.68–4.61 (m, 1H, α-CH, Phe), 4.13 (q, 2H, CH$_2$CH$_3$), 3.99–3.94 (m, 1H, α-CH, Mel), 3.77–3.59 (m, 11H, OCH$_3$ and CH$_2$-mustard), 3.17–2.82 (m, 4H, CH$_2$-Ph), 1.19 (t, 3H, CH$_2$CH$_3$). $^{13}$C NMR (CDCl$_3$) δ 171.11, 168.41 (C=O in amide and ester), 158.91 (C-4''), 146.10 (C-4'), 130.44 (2 C:s), 129.94 (2 C:s) (Ph and C-3'), 128.38 (Ph), 122.18 (C-1'), 113.67 (2 C:s) (Ph), 112.18 (2 C:s) (C-2'), 61.19 (CH$_2$CH$_3$), 54.45, 54.37, 54.29 (α-CH and OCH$_3$), 52.99 (2 C:s) (N—CH$_2$), 40.31 (2 C:s) (CH$_2$—Cl), 36.34, 36.29 (CH$_2$-Ph), 13.14 (CH$_2$CH$_3$).

Example 6

L-Melphalanyl-L-p-nitrophenylalanine ethyl ester hydrochloride (JV26)

N-tert-Butoxycarbonyl-L-p-nitrophenylalanine (395 mg; 1.27 mmol) was dissolved in HCl saturated ethanol (20 ml). The solution was heated at reflux for 20 h. The mixture was partitioned between CHCl$_3$ and 1M HCl (pH 4). The aqueous layer was basified with 5% KOH to pH 10 and was then extracted four times with CHCl$_3$. The organic layers were combined, dried (MgSO$_4$), filtered, and concentrated in vacuo to afford L-p-nitrophenylalanine ethyl ester as a thin yellowish oil (195 mg; 65%) that was used in the next step without further purification.

$^1$H NMR (CDCl$_3$) δ 8.14 (d, 2H, Ph-H), 7.37 (d, 2H, Ph-H), 4.14 (q, 2H, CH$_2$CH$_3$), 3.71 (t, 1H, α-CH), 3.16–2.91 (m, 2H, CH$_2$-Ph), 1.22 (t, 3H, CH$_2$CH$_3$).

N-tert-Butoxycarbonyl-L-melphalan (86 mg; 0.21 mmol) was dissolved in dichloromethane (3 ml). PyBOP (115 mg; 0.22 mmol) and triethylamine (58 μl; 0.42 mmol) were added. After stirring at RT for 30 minutes a solution of triethylamine (29 μl; 0.21 mmol) and L-p-nitrophenylalanine ethyl ester (55 mg; 0.23 mmol) in 3 ml dichloromethane was added. The solution was stirred at RT over night. Dichloromethane was added up to a total volume of 10 ml before extraction with 10 mL saturated aqueous NaHCO$_3$ and 10 ml 10% citric acid. The organic layer was dried (MgSO$_4$), filtered and concentrated in vacuo. The crude product was purified twice by flash column chromatography on silica using CHCl$_3$:MeOH (9:1 and 19:1) as eluent, to yield pure N-tert-butoxycarbonyl-L-melphalanyl-L-p-nitrophenylalanine ethyl ester as a light yellow solid (90 mg; 69%). Mp 152–155° C. $^1$NMR (CDCl$_3$) δ 8.09–8.02 (m, 2H, Ph-H, Phe), 7.21–7.01 (m, 4H, Ph-H), 6.57 (d, 2H, Ph-H, Mel), 6.50–6.44 (m, 1H, NH, Ph), 4.92 (br s, 1H, NH, Mel), 4.77 (br s, 1H, α-CH, Phe), 4.25 (br s, 1H, α-CH, Mel), 4.11 (q, 2H, CH$_2$CH$_3$), 3.70–3.53 (m, 8H, CH$_2$-mustard), 3.25–3.10 (m, 2H, CH$_2$-Ph, Phe), 2.97–2.84 (m, 2H, CH$_2$-Ph, Mel) 1.40 (s, 9H, CH$_3$-Boc), 1.19 (t, 3H, CH$_2$CH$_3$). $^{13}$C NMR (CDCl$_3$) δ 171.31, 170.40 (C=O in amide and ester), 155.46 (C=O, Boc), 147.14 (Ph), 145.10 (C-4'), 143.85 (Ph), 130.68 (2 C:s), 130.41(2 C:s) (Ph and C-3'), 125.21 (C-1'), 123.62 (2 C:s) (Ph), 112.40 (2 C:s) (C-2'), 80.45 (C-Boc), 61.95 (CH$_2$CH$_3$), 55.98 (α-C), 53.54 (2 C:s) (N—CH$_2$), 53.03 (α-CH), 40.46 (2 C:s) (CH$_2$—Cl), 37.86, 37.00 (CH$_2$-Ph), 28.33 (3 C:s) (CH$_3$-Boc), 14.20 (CH$_2$CH$_3$).

N-tert-Butoxycarbonyl-L-melphalanyl-L-p-nitro-phenylalanine ethyl ester (80 mg; 0.13 mmol) was dissolved in 6 ml HCl saturated ethyl acetate. The mixture was stirred at RT for 1.5 h. The solvent was removed in vacuo. The crude product was dissolved in ethanol followed by precipitation in diethyl ether to afford JV26 (55 mg; 76%) as a light orange solid. Mp: 138–142° C.

$^1$H NMR (CDCl$_3$) δ 8.20–8.06 (m, 2H, Ph-H, Phe), 7.52–7.33 (m, 2H, Ph-H, Phe), 7.17–6.85 (m, 2H, Ph-H, Mel), 6.77–6.60 (m, 2H, Ph-H, Mel), 4.16 (q, 2H, CH$_2$CH$_3$), 4.00–3.94 (m, 1H, α-CH, Mel), 3.79–3.54 (m, 8H, CH$_2$-mustard), 3.19–2.71 (m, 4H, CH$_2$-Ph), 1.21 (t, 3H, CH$_2$CH$_3$). $^{13}$C NMR (CDCl$_3$) δ 170.46, 168.29 (C=O in amide and ester), 147.16 (Ph), 145.61 (C-4'), 144.67 (Ph), 130.96 (2 C:s), 130.24 (2 C:s) (Ph and C-3'), 126.72 (C-1'), 123.26 (2 C:s) (Ph), 115.45 (2 C:s) (C-2'), 61.53 (CH$_2$CH$_3$), 54.76, 54.08 (α-CH), 53.54 (2 C:s) (N—CH$_4$), 39.22 (2 C:s) (CH$_2$—Cl), 36.75, 36.33 (CH$_2$-Ph), 13.16 (CH$_2$CH$_3$).

Example 7

L-Melphalanyl-L-melphalan ethyl ester hydrochloride (JV27)

N-tert-Butoxycarbonyl-L-melphalan (35 mg; 86 μmol) was dissolved in dichloromethane (2 ml). PyBOP (43 mg; 83 μmol) and triethylamine (23 μl; 162 μmol) were added. After stirring at RT for 30 minutes a solution of triethylamine (23 μl; 162 μmol) and L-melphalan ethyl ester hydrochloride (32 mg; 87 μmol) in 2 ml dichloromethane was added. The solution was stirred at RT over night, and more dichloromethane (up to 10 ml) was added before extraction with 10 ml saturated aqueous NaHCO$_3$ and 10 ml 10% citric acid. The organic layer was dried (MgSO$_4$), filtered and concentrated in vacuo. Purification by column chromatography on silica using CHCl$_3$:MeOH:heptane (4:1:7) and CHCl$_3$:MeOH (19:1) as eluents gave pure N-tert-butoxycarbonyl-L-melphalanyl-L-melphalan-ethyl ester as a brown gum (29 mg; 49%).

$^1$H NMR (CDCl$_3$) δ 7.06 (d, 2H, Ph-H), 6.87 (d, 2H, Ph-H), 6.61–6.46 (m, 4H, Ph-H), 6.24 (br s, 1H, NH), 4.99 (br s, 1H, NH), 4.68 (br s, 1H, α-CH), 4.25 (br s, 1H, α-CH), 4.12 (q, 2H, CH$_2$CH$_3$), 3.72–3.47 (m, 16H, CH$_2$-mustard), 3.02–2.87 (m, 4H, CH$_2$-Ph), 1.40 (s, 9H, CH$_3$-Boc), 1.21 (t, 3H, CH$_2$CH$_3$). $^{13}$C NMR (CDCl$_3$) δ 171.16, 170.71 (C=O in amide and ester), 154.87 (C=O, Boc), 145.19 (2 C:s) (C-4' and C-4''), 130.79 (2 C:s), 130.68 (2 C:s) (C-3' and C-3''), 125.08, 124.33 (C-1', C-1''), 112.30 (2 C:s), 112.04 (2 C:s) (C-2' and C-2''), 79.65 (C-Boc), 61.50 (CH$_2$CH$_3$), 55.83 (α-CH), 53.57 (2 C:s) (N—CH$_2$), 53.53 (α-CH), 40.55, 40.47 (CH$_2$—Cl), 37.04, 36.98 (CH$_2$-Ph), 28.36 (3 C:s) (CH$_3$-Boc), 14.24 (CH$_2$CH$_3$).

N-tert-Butoxycarbonyl-L-melphalanyl-L-melphalan ethyl ester (20 mg; 28 μmol) was dissolved in 3 ml HCl saturated ethyl acetate. The mixture was stirred at RT for 1.5 h. The solvent was removed in vacuo. The crude product was dissolved in ethanol followed by precipitation in diethyl ether to afford JV27 (11 mg; 62%) as a light brown solid.

Mp: 157–160° C. $^1$H NMR (CDCl$_3$) δ 7.19–7.01 (m, 4H, Ph-H), 6.80–6.63 (m, 4H, Ph-H), 4.66–4.61 (m, 1H, α-CH), 4.13 (q, 2H, CH$_2$CH$_3$), 4.02–3.96 (m, 1H, α-CH), 3.83–3.54 (m, 16H, 8 CH$_2$-mustard), 3.18–2.81 (m, 4H, CH$_2$-Ph), 1.17 (t, 3H, CH$_2$CH$_3$).

Example 8

L-Melphalanyl-L-p-fluorophenylalanine isopropyl ester hydrochloride (JV28)

L-p-Fluorophenylalanine (266 mg, 1.45 mmol) was dissolved in HCl saturated isopropanol (10 ml). The solution was heated at reflux for 2.5 h. The solvent was evaporated to yield the product as a white cottonlike solid (350 mg, 91%). The product was used in the next step without further purification. Mp 226–229° C.

$^1$H NMR (CD$_3$OD) δ 7.31–7.23 (m, 2H, Ph-H), 7.12–7.03 (m, 2H, Ph-H), 5.10–5.00 (m, 1H, CH-isopropyl), 4.22 (t, 1H, α-CH), 3.22–3.11 (m, 2H, CH$_2$-Ph), 1.25 (d, 3H, CH$_3$-isopropyl), 1.18 (d, 3H, CH$_3$-isopropyl).

N-tert-Butoxycarbonyl-L-melphalan (52 mg; 0.13 mmol) was dissolved in dichloromethane (2 ml). PyBOP (71 mg, 0.14 mmol) and triethylamine (38 μl; 0.27 mmol) were added. After stirring at RT for 30 minutes a solution of triethylamine (38 μl; 0.27 mmol) and L-p-fluorophenylalanine isopropyl ester (39 mg; 0.15 mmol) in 2 ml dichloromethane was added. The solution was stirred at RT over night. Dichloromethane was added up to a total volume of 10 ml before extraction with 10 ml saturated aqueous NaHCO$_3$ and 10 m 10% citric acid. The organic layer was dried (MgSO$_4$), filtered and concentrated in vacuo. The crude product was purified by flash column chromatography on silica using CHCl$_3$:MeOH (19:1) as eluent, to yield pure N-tert-butoxycarbonyl-L-melphalanyl-L-p-fluorophenylalanine isopropyl ester as a weakly orange semisolid (57 mg; 71%).

$^1$H NMR (CDCl$_3$) δ 7.06–6.85 (m, 6H, Ph-H), 6.56 (d, 2H, Ph-H, Mel), 6.40 (br s, 1H, NH, Phe), 5.00–4.85 (m, 2H, CH-isopropyl, NH, Mel), 4.68 (br s, 1H, α-CH, Phe), 4.27 (br s, 1H, α-CH, Mel), 3.69–3.52 (m, 8H, CH$_2$-mustard), 3.02–2.85 (m, 4H, CH$_2$-Ph), 1.37 (s, 9H, CH$_3$-Boc), 1.18 (d, 3H, CH$_3$-isopropyl), 1.14 (d, 3H, CH$_3$-isopropyl). $^{13}$C NMR (CDCl$_3$) δ 171.00, 170.43 (C=O in amide and ester), 161.95 (d, J=245.0 Hz, C-4"), 155.35 (C=O, Boc), 145.12 (C-4'), 131.60 (C-1"), 130.99 (2 C:s) (d, J=7.75 Hz, C-2"), 130.72 (2 C:s) (C-3'), 125.26 (C-1'), 115.29 (2 C:s) (d, J=20.6 Hz, C-3"), 112.27 (2 C:s) (C-2'), 80.24 (C-Boc), 69.52 (CH-isopropyl), 55.82 (α-CH), 53.53 (2 C:s) (N—CH$_2$), 53.40 (α-CH), 40.48 (2 C:s) (CH$_2$—Cl), 37.29 (2 C:s) (CH$_2$-Ph), 28.33 (3 C:s) (CH$_3$-Boc), 21.81, 21.73 (CH$_3$-isopropyl).

N-tert-Butoxycarbonyl-L-melphalanyl-L-p-fluoro-phenylalanine isopropyl ester (48 mg; 79 μmol) was dissolved in 4 ml HCl saturated ethyl acetate. The mixture was stirred at RT for 30 minutes. The solvent was removed in vacuo. The crude product was dissolved in ethanol followed by precipitation in diethyl ether to afford JV28 (22 mg; 50%) as a white solid. Mp: 192–195° C.

$^1$H NMR (CDCl$_3$) δ 7.28–7.17 (m, 2H, Ph-H, Phe), 7.14 (d, 2H, Ph-H, Phe), 7.04–6.96 (m, 2H, Ph-H, Mel), 6.76–6.67 (m, 2H, Ph-H, Mel), 4.68–4.60 (m, 1H, α-CH, Phe), 4.00–3.93 (m, 1H, α-CH, Mel), 3.76–3.58 (m, 8H, CH$_2$-mustard), 3.18–2.80 (m, 4H, CH$_2$-Ph), 1.24 (d, 3H, CH$_3$-isopropyl), 1.15 (d, 3H, CH$_3$-isopropyl). $^{13}$C NMR (CDCl$_3$) δ 170.49, 168.42 (C=O in amide and ester), 162.06 (d, J=242.4 Hz, C-4"), 146.13 (C-4'), 132.48 (C-1"), 130.72 (2 C:s) (d, J=7.64 Hz, C-2"), 130.40 (2 C:s) (C-3'), 122.10 (C-1'), 114.87 (2 C:s) (d, J=21.2 Hz, C-3"), 112.45 (2 C:s) (C-2'), 69.27 (CH-isopropyl), 54.28 (2 C:s) (α-CH), 52.97 (2 C:s) (N—CH$_2$), 40.26 (2 C:s) (CH$_2$—Cl), 36.31 (2 C:s) (CH$_2$-Ph), 20.70, 20.56 (CH$_3$-isopropyl).

Example 9

L-Melphalanyl-L-p-aminophenylalanine ethyl ester hydrochloride (JV29)

N-tert-Butoxycarbonyl-L-p-nitrophenylalanine (510 mg; 1.64 mmol) was dissolved in 80% ethanol (12.5 ml). A solution of CaCl$_2$ (150 mg; 1.35 mmol) in water (1 ml) was added together with powdered zinc (3.79 g; 58 mmol). After heating at reflux for 3.5 h the suspension was filtered and the zinc powder was rinsed with excess ethanol. The filtrate was concentrated in vacuo to afford 600 mg (130%) of N-tert-butoxycarbonyl-L-p-aminophenylalanine as a light yellow solid which still contained some ethanol. The product was used in the next step without further purification.

$^1$H NMR (CD$_3$OD) δ 6.96 (d, 2H, Ph-H), 6.63 (d, 2H, Ph-H), 4.16–4.07 (m, 1H, α-CH), 3.05–2.76 (m, 2H, CH$_2$-Ph), 1.38 (s, 9H, CH$_3$-Boc).

N-tert-Butoxycarbonyl-L-p-aminophenylalanine (201 mg; 0.72 mmol) was dissolved in HCl saturated ethanol (10 ml). The solution was heated at reflux for 3 h. The mixture was partitioned between CHCl$_3$ and 1M HCl (pH 4). The aqueous layer was basified with 5% KOH to pH 10 and was then extracted four times with CHCl$_3$. The organic layers were combined, dried (MgSO$_4$), filtered, and concentrated in vacuo to afford L-p-aminophenylalanine ethyl ester as a yellowish oil (90 mg; 60%) which was used in the next step without further purification.

$^1$H NMR (CDCl$_3$) δ 6.97 (d, 2H, Ph-H), 6.61 (d, 2H, Ph-H), 4.13 (q, 2H, CH$_2$CH$_3$), 3.71 (t, 1H, α-CH), 3.04–2.78 (m, 2H, CH$_2$-Ph), 1.23 (t, 3H, CH$_2$CH$_3$).

N-tert-Butoxycarbonyl-L-melphalan, (44 mg; 0.11 mmol) was dissolved in dichloromethane (2 ml). PyBOP (55 mg; 0.11 mmol) and triethylamine (28 μl; 0.20 mmol) were added. After stirring at RT for 30 minutes a solution of triethylamine (14 μl; 0.10 mmol) and L-p-aminophenylalanine ethyl ester (21 mg; 0.10 mmol) in 2 ml dichloromethane was added. The solution was stirred at RT over night. Dichloromethane was added up to a total volume of 10 ml before extraction with 10 ml saturated aqueous NaHCO$_3$ and 10 ml 10% citric acid. The organic layer was dried (MgSO$_4$), filtered and concentrated in vacuo. The crude product was purified twice by flash column chromatography on silica using CHCl$_3$:MeOH (9:1and 19:1) as eluents, to afford N-tert-butoxycarbonyl-L-melphalanyl-L-p-aminophenylalanine ethyl ester as a brown-orange oil (28 mg; 47%).

$^1$H NMR (CDCl$_3$) δ 7.03 (d, 2H, Ph-H, Mel), 6.75 (d, 2H, Ph-H; Phe), 6.59–6.52 (m, 4H, Ph-H), 6.26 (br s, 1H, NH, Phe), 4.96 (br s, 1H, NH, Mel), 4.68 (br s, 1H, α-CH, Phe), 4.26 (br s, 1H, α-CH, Mel), 4.10 (q, 2H, CH$_2$CH$_3$), 3.70–3.53 (m, 8H, CH$_2$-mustard), 2.97–2.88 (m, 4H, CH$_2$-Ph), 1.38 (s, 9H, CH$_3$-Boc), 1.19 (t, 3H, CH$_2$CH$_3$). $^{13}$C NMR (CDCl$_3$) δ 171.21, 170.83 (C=O in amide and ester), 145.37, 144.96 (C-4', C-4"), 130.78 (3 C:s), 130.21 (2 C:s) (Ph and C-3'), 125.37 (C-1'), 115.22 (2 C:s) (Ph), 112.26 (2 C:s) (C-2'), 80.09 (C-Boc), 61.42 (CH$_2$CH$_3$), 55.61 (α-CH), 53.56 (2 C:s) (N—CH$_2$), 53.48 (α-CH), 40.56 (2 C:s) (CH$_2$—Cl), 37.37, 37.17 (CH$_2$-Ph), 28.34 (3 C:s) (CH$_3$-Boc), 14.21 (CH$_2$CH$_3$).

N-tert-Butoxycarbonyl-L-melphalanyl-L-p-amino-phenylalanine ethyl ester (20 mg; 34 μmol) was dissolved in 3 ml HCl saturated ethyl acetate. The mixture was stirred at RT for 30 minutes. The solvent was removed in vacuo. The crude product was dissolved in ethanol followed by precipitation in diethyl ether to afford JV29 (4 mg; 22%) as a light brown solid.

$^1$H NMR (CDCl$_3$) δ 7.46–7.29 (m, 4H, Ph-H, Phe), 7.18–7.07 (m, 2H, Ph-H, Mel), 6.78–6.66 (m, 2H, Ph-H, Mel), 4.73–4.66 (m, 1H, α-CH, Phe), 4.10 (q, 2H, CH$_2$CH$_3$), 4.06–3.99 (m, 1H, α-CH, Mel), 3.79–3.56 (m, 8H, CH$_2$-mustard), 3.22–2.83 (m, 4H, CH$_2$-Ph), 1.15 (t, 3H, CH$_2$CH$_3$).

Example 10

L-Melphalanyl-D-phenylalanine ethyl ester (T4)

D-Phenylalanine (250 mg, 1.52 mmol) was dissolved in 5 ml EtOH previously bubbled in HCl (gas). The solution was brought to 100° C. and allowed to reflux overnight. The solvent was evaporated off affording 280 mg crude product. Recrystallization from EtOH/EtOAc/pentane gave 239 mg (81% yield) of D-phenylalanine ethyl ester as white crystals.
$^1$H NMR (CD$_3$OD) δ 7.4–7.22 (m, 5H, Ph-H), 4.31–4.14 (m, 3H, CH$_2$CH$_3$, α-H), 3.35–3.08 (m, 2H, CH$_2$-Ph), 1.25–1.20 (t, 3H, CH$_2$CH$_3$).

N-tert-Butoxycarbonyl-L-melphalan (65 mg, 0.16 mmol), D-phenylalanine ethyl ester (53 mg, 0.23 mmol), HOBT (32 mg, 0.24 mmol), and NMM (25 μl, 0.23 mmol) were dissolved in 4 ml dichloromethane. This solution was cooled to 0° C. and EDC (44 mg, 0.23 mmol) was added. The solution was stirred for 0.5 h at 0° C. and then for 3 h at RT. The reaction mixture was then diluted to 20 ml with dichloromethane and the reaction stopped by successive extractions with 10% aqueous citric acid (25 ml), saturated NaHCO$_3$ (25 ml) and brine (25 ml). The organic phase was then dried over anhydrous Na$_2$SO$_4$ and the solvent evaporated off under reduced pressure to give 60 mg of a yellow oil. The crude product was then separated by flash chromatography using a gradient eluent system of ether:pentane (2:3→1:1→1:0). The pure fractions were collected and the solvent evaporated off to afford 25 mg (25%) of N-tert-butoxycarbonyl-L-melphalanyl-D-phenylalanine ethyl ester as white crystals.

N-tert-Butoxycarbonyl-L-melphalanyl-D-phenylalanine ethyl ester (90 mg, 0.16 mmol) was dissolved in 5 ml EtOAc previously bubbled with HCl (gas). The mixture was stirred at RT for 30 minutes. The solvent was removed in vacuo. The residue was recrystallized from EtOH/Et$_2$O. L-Melphalanyl-D-phenylalanine ethyl ester hydrochloride (T4) was isolated as white crystals in 62% yield (46 mg).

Comparative Example

N-Acetyl-L-melphalanyl-L-p-fluorophenylalanine ethyl ester (AcJ1)

L-Melphalanyl-L-p-fluorophenylalanine ethyl ester hydrochloride (10 mg, 0.019 mmol), was dissolved in dichloromethane (0.5 ml) and pyridine (4 μl, 0.044 mmol) was added. Acetic anhydride (2. μL, 0.22 mmol) was added and the mixture was stirred for 1 h at RT. More pyridine (2 μl, 0.022 mmol) and acetic anhydride (2. μl, 0.22 mmol) were added and a clear solution was obtained after stirring for one hour. The solution was extracted with 10% aqueous citric acid and brine. The organic phase was dried over anhydrous Na$_2$SO$_4$ and the solvent evaporated off under reduced pressure. The solid residue was recrystallized in EtOH/diethyl ether to afford AcJ1 as white crystals.

$^1$H NMR: (CDCl$_3$) δ 7.09–6.90 (m, 6H, Ph-H, Phe, Mel), 6.60 (d, 2H, Ph-H, Mel), 6.25 (br d, 1H, NH), 6.04 (br d, 1H, NH), 4.73 (dd, 1H, α-CH), 4.55 (dd, 1H, α-CH), 4.14 (q, 2H; CH$_2$CH$_3$), 3.76–3.58 (m, 8H, CH$_2$-mustard), 3.12–2.88 (m, 4H, CH$_2$-Ph), 1.98 (s, 3H, CH$_3$CO), 1.22 (t, 3H, CH$_2$CH$_3$).

Biological Tests

In the following tests the cytostatic activity of the peptides of the invention was analysed and compared to the activity of melphalan (as the hydrochloride, Alkeran injection substance, Glaxo Wellcome), P2 (L-prolyl-m-L-sarcolysyl-p-L-fluorophenylalanine ethyl ester hydrochloride; from Istituto Sieroterapico Milanese, Milan, Italy), sarcolysine (Istituto Sieroterapico Milanese, Milan, Italy) and a number of standard drugs in different primary cultures of human tumor cells from patients (PHTC) and human tumor cell lines. The standard drugs tested were AraC (Cytosar), 5-FU (Flurablastin) and doxorubicin (Adramycin) from Pharmacia & Upjohn, vincristine (Oncovin) and vinorelbine (Navelbine) from Pierre Fabre, docetaxel (Taxotere) from Rhone Poulenc Rorer, cisplatin (Platinol) and etoposide (Vepesid) from Bristol-Myers Squibb, and topotecan from SmithKline Beecham.

The fluorometric microculture cytotoxicity assay (FMCA) (Larsson, R., et al-1992: Int J Cancer, 50, 177–185) was used to evaluate the compounds. Briefly, 96-well microtiter plates (NUNC, Roskilde, Denmark) are prepared with 20 μl drug solution at ten times the desired concentration and stored for up to two months at −70° C. In general the substances are first dissolved in absolute or acidic ethanol to concentrations of 4.0 to 8.2 mM and further diluted with sterile water or sterile phosphate buffered saline (PBS, Sigma chemicals). All dilutions with water are made directly before the experiments to minimise the influence of mustard hydrolysis. Final ethanol concentrations do not exceed 1% v/v. At day zero of the experiment 180 μl of cell suspension of adequate concentration is added to the wells of the thawed plate, six wells serve as controls (cell suspension only) and six wells as blanks (cell medium only). After 72 hours incubation the cells are washed once with PBS, and 100 μl of fluorescein diacetate (10 μg/ml) in a physiological buffer is added. After another 45 min the generated fluorescence (ex 485 nm; em 528 nm) is measured in a 96-well scanning fluorometer (Fluoroscan II, Labsystems Oy, Helsinki, Finland). The generated fluorescence is proportional to the number of living cells, and data are presented as survival index (fluorescence in test well in percent of control wells with blank values subtracted) and IC50 (inhibitory concentration 50%, as calculated by the software GraphPad Prism® (Graphpad Software Inc., San Diego, Calif., USA)). Quality criteria for a successful assay include a coefficient of variation less than 30% in blank (six wells), control (six wells) and test wells (three) respectively, a control signal more than ten times the blank and finally an initial cell viability of more than 70% (primary human tumour cultures) or 90% (cell lines) as judged by the trypan blue exclusion test.

Fluorescein diacetate (FDA, Sigma) was dissolved in DMSO to 10 mg/ml and kept frozen as a stock solution in the dark. Cell growth medium RPMI-1640 (Sigma) supplemented with 10% heat-inactivated fetal calf serum (FCS, Sigma chemical Co., St. Louis, Mo.), 2 mM glutamine, 100 μg/ml streptomycin, and 100 μg/ml penicillin, was used.

Much work with FMCA has focused on prediction of clinical activity of anticancer drugs for individual patients. The predictive ability of this assay for this application has been shown to be comparable to that of many other clinically accepted test procedures with sensitivity and specificity in the range of 80–90, and 60–70, respectively.

Test 1. Cytotoxic Activity in Fresh Human Tumour Specimens

The cytotoxic activity of melphalan, P2 (L-prolyl-m-L-sarcolysyl-p-L-fluorophenylalanine ethyl ester hydrochloride) and J1 (L-melphalanyl-p-L-fluorophenylalanine ethyl ester hydrochloride) on human tumour samples was compared using the fluorometric microculture cytotoxicity assay (FMCA). Each drug was tested in six concentrations ranging from 82 to 0.131 $\mu$M, each concentration in triplicate.

Figure 1:
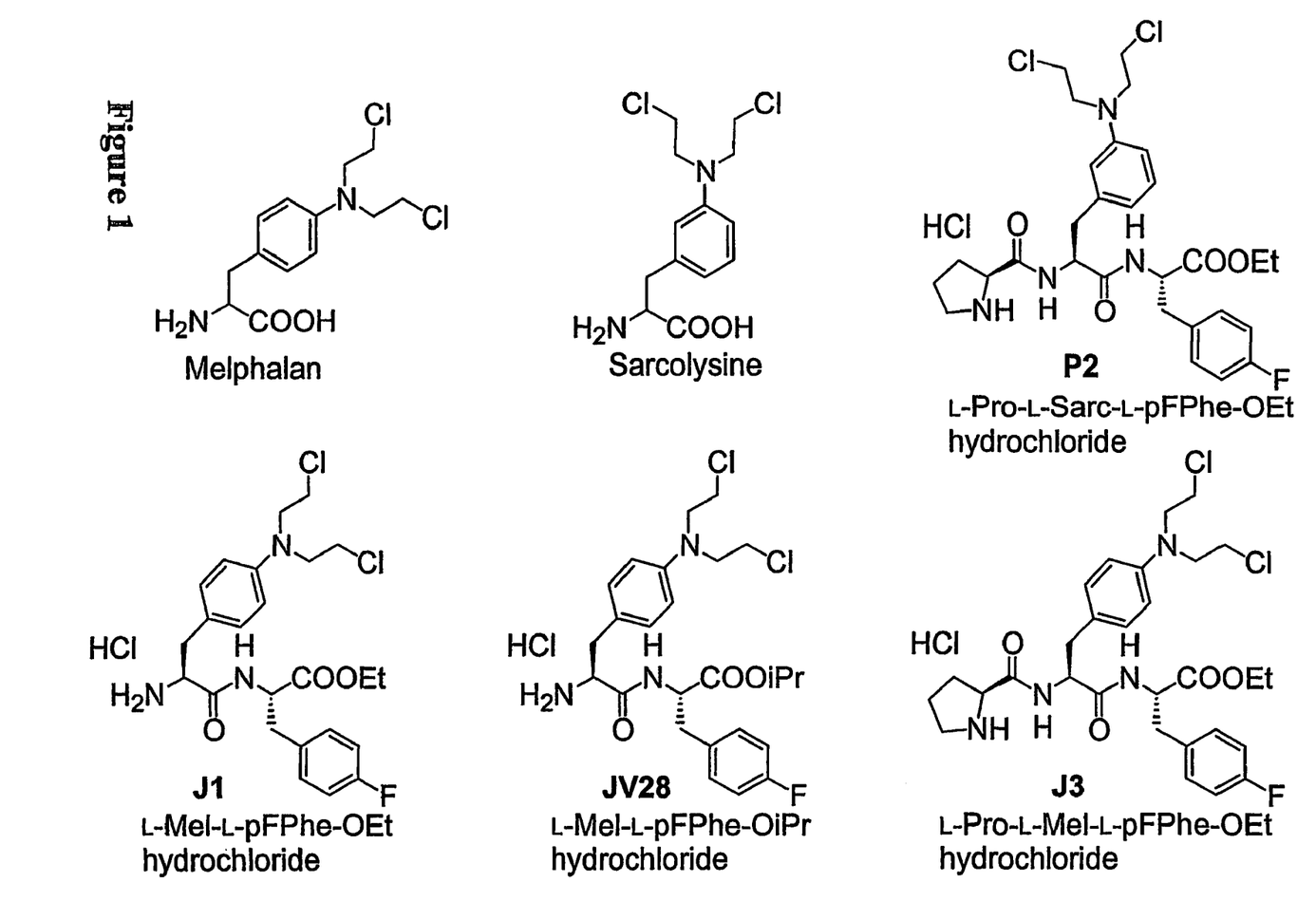
FIG. 1 shows the chemical formulas of the known compounds melphalan, sarcolysine and P2, as well as the formulas of the compuonds of the invention J1, J3, and JV28.
Figure 2:
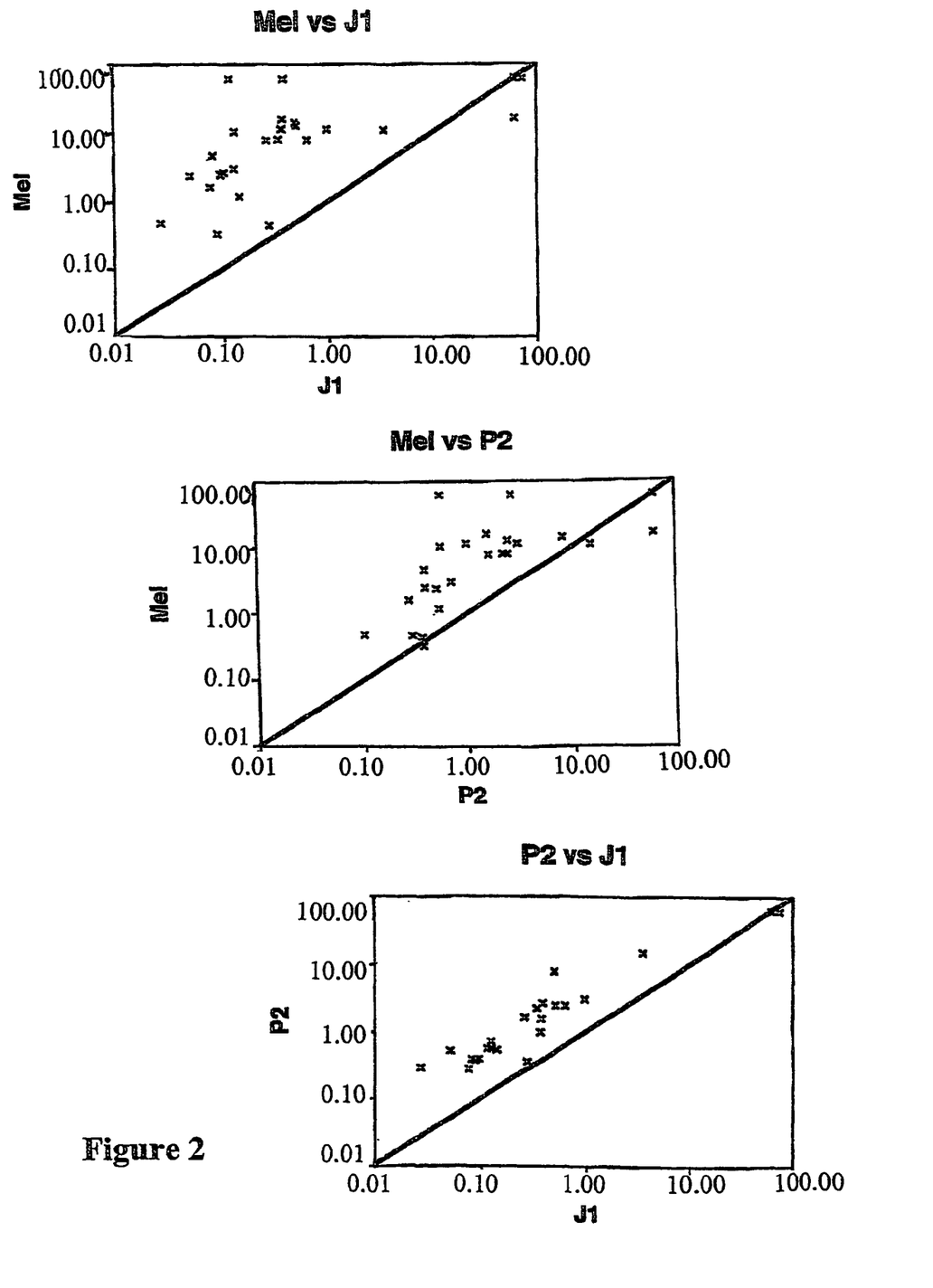
FIG. 2 shows a comparison of IC50s for melphalan, J1 and P2 in 27 human tumour samples.

In total twenty-seven fresh human tumour specimens were analysed, these were of different origin: fourteen hematological (of which at least five were previously treated with cytotoxic drugs in the clinic) and thirteen solid tumour (five previously treated) samples were analysed. Concentration-response curves were plotted and the IC50s were determined. The results are presented in FIG. 2, wherein the diagonal solid lines represent equipotency, and dots above this line favour the drug on the x-axis and vice versa. The result shows that J1 in all cases was more active than P2, which in turn was more active than melphalan.

Using the same FMCA assay the cytotoxic activity of melphalan, P2 and J1 was again tested, this time on in total sixty-four fresh human tumour specimens. The tumours were of different origin: forty-two hematological and twenty-two solid tumour samples were analysed. In parallel the activity of some clinically well known and used standard substances was assayed at concentrations of from 0.92 to 10.3 $\mu$M. The standard drugs were araC, vincristin, vinorelbine, docetaxel, cisplatin, doxorubicin, and etoposide. A comparison of the activities is presented as survival index at a defined concentration in Table 1 below. J1 shows a superior activity at 0.66 $\mu$M.

TABLE 1

Activity of J1, melphalan, P2 and standard drugs in PHTC

| Drug | Concentration $\mu$M | Tumor cell survival index % | |
|---|---|---|---|
| | | Hematological (n = 42) | Solid (n = 22) |
| J1 | 0.66 | 13.7 | 46.9 |
| Melphalan | 3.3 | 41 | 88.8 |
| P2 | 0.66 | 34.7 | 86.0 |
| AraC | 10.3 | — | 102 |
| Vincristine | 3.0 | 39 | 93 |
| Vinorelbine | 3.1 | 50 | 73 |
| Docetaxel | 6.2 | — | 67 |
| Cisplatin | 6.7 | 63 | 79 |
| Doxorubicin | 0.92 | 29 | 97 |
| Etoposide | 8.5 | 47 | 81 |

Test 2. Cytotoxic Activity in a Panel of Ten Human Tumour Cell Lines

The cytotoxic activity of nine different peptides of the invention (prepared in Examples 1–9) was compared with melphalan, P2 (L-prolyl-m-L-sarcolysyl-p-L-fluorophenylalanine ethyl ester hydrochloride), sarcolysine, and the standard drugs doxorubicin, vincristine, cisplatin, 5-Fu, and topotecan in ten cell lines using the FMCA method. Each drug was tested in six concentrations ranging from 40 to 0.013 $\mu$M (melphalan from 1.6 mM to 0.51 $\mu$M), and each concentration in duplicate. The experiment was repeated three times and all survival data were then used to calculate IC50 for each drug on each cell line.

The selection of cells in the cell line panel has been described earlier (Dhar, S., et al. 1996: Br J Cancer, 74, 888–896). Four parental lines of different origin (lymphoma U-937 GBT; myeloma RPMI 8226; small cell lung cancer NCI-H69; and leukemia CCRF-CEM), five sublines selected for various drugs, and one primary resistant cell line (renal carcinoma ACHN) was included. The subline U-937-vcr is selected for vincristine resistance, subline 8226Dox40 and H69AR for doxorubicin resistance, subline 8226LR5 for melphalan resistance. The cell line growth and morphology were monitored on a weekly basis, resistance every two or three months.

The results are presented in Table 2 and show that the cytotoxic activity varies among the peptides and compare favourably with melphalan, m-L-sarcolysine and P2. In addition some of the peptides show higher activities on certain cell lines than some of the tested standard chemotherapeutic substances.

TABLE 2

Activity of peptides of the invention compared to melphalan, sarcolysine, P2 and standard drugs in a cell line panel representing defined forms of cytotoxic drug resistance, IC50 ($\mu$M)

| Cell line | J1 | J3 | JV22 | JV24 | JV25 | JV26 | JV27 | JV28 | JV29 |
|---|---|---|---|---|---|---|---|---|---|
| CEM/S | 0.03 | 0.06 | 0.02 | 0.05 | 0.04 | 0.05 | 0.14 | 0.06 | 0.06 |
| CEM/R | 0.01 | 0.02 | 0.01 | 0.03 | 0.02 | 0.03 | 0.1 | 0.04 | 0.03 |
| ACHN | 0.4 | 1.72 | 0.17 | 0.32 | 0.2 | 0.22 | 0.21 | 0.05 | 0.19 |
| H69 | 0.04 | 0.2 | 0.04 | 0.08 | 0.04 | 0.06 | 0.29 | 0.05 | 0.09 |
| H69AR | 0.9 | 1.36 | 0.39 | 0.48 | 0.28 | 0.51 | 1.4 | 0.37 | 0.46 |
| 8226S | 0.81 | 1.51 | 0.67 | 1.11 | 0.65 | 1.05 | 1.01 | 0.51 | 0.9 |
| 8226Dox40 | 1.76 | 5.66 | 1.38 | 5.54 | 1.2 | 1.73 | 1.58 | 0.89 | 2.01 |
| 8226LR5 | 2.47 | 3.52 | 1.86 | 2.5 | 1.82 | 1.99 | 2.46 | 1.88 | 2.73 |
| U937gtb | 0.07 | 0.23 | 0.14 | 0.2 | 0.15 | 0.23 | 0.16 | 0.1 | 0.15 |

TABLE 2-continued

Activity of peptides of the invention compared to melphalan, sarcolysine, P2 and standard drugs in a cell line panel representing defined forms of cytotoxic drug resistance, IC50 (μM)

| U937vcr | 0.11 | 0.42 | 0.13 | 0.21 | 0.16 | 0.26 | 0.26 | 0.15 | 0.19 |
|---|---|---|---|---|---|---|---|---|---|
| MEAN | 0.66 | 1.47 | 0.48 | 1.05 | 0.46 | 0.61 | 0.76 | 0.41 | 0.68 |

| Cell line | Melphalan | P2 | Sarcolysine | Doxorubicin | Vincristine | Cisplatin | 5-FU | Topotecan |
|---|---|---|---|---|---|---|---|---|
| CEM/S | 1.48 | 0.94 | 2.54 | 0.18 | 0.08 | 2.50 | 57.4 | 0.02 |
| CEM/R | 0.94 | 0.63 | 1.70 | 1.31 | 0.01 | 1.87 | 44.5 | 0.02 |
| ACHN | 133.32 | 4.59 | 390 | 14.2 | 109 | 17.8 | 769 | 16.3 |
| H69 | 13.44 | 4.59 | 41.15 | 1.66 | 69.8 | 92.47 | 769 | 1.72 |
| H69AR | 48.74 | 4.27 | 61.4 | 11.6 | 121 | 13.5 | 769 | 180.5 |
| 8226S | 10.82 | 5.11 | 30.4 | 0.13 | 0.01 | 14.8 | 75.6 | 0.87 |
| 8226Dox40 | 35.18 | 5.43 | 41.38 | 4.97 | 0.9 | 15.66 | 60.6 | 0.59 |
| 8226LR5 | 30.61 | 7.4 | 31.88 | 0.55 | 0.08 | 16.33 | 5.30 | 0.21 |
| U937gtb | 1.8 | 1.78 | 3.78 | 0.11 | 0.01 | 2.57 | 88.4 | 0.02 |
| U937vcr | 2.95 | 1.77 | 6.64 | 0.42 | 0.08 | 3.0 | 572.0 | 0.02 |
| MEAN | 27.93 | 3.35 | 61.09 | 3.51 | 30.1 | 18.0 | 321 | 20.0 |

Test 3. Cytotoxic Activity of J1 in Lung Cancer Cell Lines

J1 was also tested against a panel of lung cancer cell lines and compared with melphalan and some standard chemotherapeutic agents using the FMCA. In total four small cell lung cancer cell lines (U-1906 L and E, U-1285, and U-1690) and seven non-small cell lung cancer cell lines (NCI-H23, U-1752, NCI-H611, NCI-H157, U-1810, NCI-H125 and U-1568) were analyzed. The results are presented in Table 3.

TABLE 3

Cytotoxic activity in lung cell cancer lines, IC50 (μM)

| Cell line | J1 | Melphalan | Cis-platin | Doxo-rubicin | Docetaxel | Topotecan |
|---|---|---|---|---|---|---|
| NCI-H23 | 7.6 | 125 | 11.6 | 0.14 | 1.5 | 5.84 |
| U-1752 | 1.3 | 39.3 | 11.7 | 0.42 | 0.46 | 28.0 |
| NCI-H611 | 3.17 | 78.3 | 50.7 | 183 | 1.1 | 236 |
| NCI-H157 | 3.9 | 125 | 27.0 | 0.2 | 0.1 | 4.33 |
| U-1810 | 0.01 | 1.0 | 10.3 | 22.8 | 0.1 | 0.08 |
| NCI-H125 | 9.73 | 85.2 | 7.0 | 0.5 | 0.16 | 236 |
| U-1568 | 1.64 | 34.7 | 23.4 | 183 | 5.94 | 115 |
| U1906L | 0.22 | 36.7 | 12.2 | 0.92 | 0.1 | 0.12 |
| U1285 | 0.04 | 1.97 | 2.93 | 0.52 | 0.1 | 0.17 |
| U-1906E | 1.17 | 20.9 | 21.1 | 0.44 | 0.1 | 0.08 |
| U1690 | 1.39 | 12.4 | 6.73 | 2.21 | 7.7 | 0.92 |

The results show that J1 on a molar basis compares favourably with melphalan and most standard agents used in the clinical therapy of lung cancer and also shows an overall activity similar to that observed for docetaxel, a tubulin active drug which lately has been introduced into lung cancer therapy. Since J1 and other melphalan derivatives are non-cross resistant with taxanes (judged from correlation analysis of the activity patterns) these two drug classes may form attractive treatment combinations.

Test 4. Cytotoxic Activity of J3 and JV28 in Primary Cultures of Human Tumor Cells from Patients (PHTC)

In another set of experiments the activity of J1, J3 and JV28 was compared with that of melphalan, sarcolysine and P2 in 31 PHTC cultures using the FMCA. The results are presented in Table 4.

TABLE 4

Cytotoxic activity of drugs in PHTC

| | | Tumor cell survival index (%) | | |
|---|---|---|---|---|
| Drug | Conc. μM | Hematological tumors n = 7–11 | Solid tumors n = 12–20 | Total n = 19–31 |
| J3 | 4 | 7 | 36.3 | 25.9 |
| JV28 | 4 | 6.7 | 44.2 | 30.4 |
| J1 | 4 | 6.6 | 56.5 | 40.9 |
| Melphalan | 10 | 47.6 | 91.0 | 73.4 |
| Sarcolysine | 10 | 47.1 | 93.2 | 76.2 |
| P2 | 4 | 7 | 68.9 | 46.1 |

The results show that J3 and JV28 were significantly (P<0.001 Students t-test) more active against hematological PHTC samples than both melphalan and sarcolysine. J3 and JV28 were also significantly (P<0.01) more active against solid tumor samples compared not only to melphalan and sarcolysine but also compared to P2. The difference between J1 and melphalan as well as sarcolysine and P2 was statistically significant for both hematological and solid tumours. The results demonstrates an unexpectedly high activity of the new peptides against solid tumours as a group which was not shared by the reference compounds.

Test 5. Cytotoxic Activity in Different Tumour Models

The tumour type specific spectrum of antitumour activity was analysed in cell lines and primary cultures of human tumour cells from patients. Although melphalan has been classified as active against all hematological diagnoses no activity, i.e. <50% reduction in tumour cell survival, was observed against the solid tumour types. J3. J1 and JV28, on the other hand, showed activity against several types of solid tumours including breast cancer, ovarian carcinoma and lung cancer. The difference in tumor type specific activity between J1, J3 and JV 28 versus P2 is depicted in Table 5.

TABLE 5

Cytotoxic activity in different tumor models

| Tumor cell system | Number | Median response at 4.0 μM >50% reduction in tumor cell survival | | | |
|---|---|---|---|---|---|
| | | P2 | J1 | J3 | JV28 |
| Ovarian carcinoma | 8 | No | Yes | Yes | Yes |
| Breast cancer | 4 | No | Yes | Yes | Yes |
| NSC Lung cancer | 8 | No | Yes | Yes | Yes |
| Prostate cancer | 1 | No | not done | Yes | Yes |
| Corpus cancer | 4 | No | No | Yes | not done |
| Adenocarcinoma | 5 | No | Yes | Yes | Yes |

Whereas P2 was determined inactive in the listed diagnoses of Table 5, J3 was found active. J1 and JV28 were found to be active in most of these diagnoses. These data show that the tumour type specific spectrum of activity for J1, J3 and JV28 is broader than for the reference compounds and includes important types of solid tumours.

Test 6. Circumvention of Melphalan Resistance

The ability to circumvent melphalan resistance was investigated in 27 PHTC samples from 9 patients with hematological and 18 patients with solid tumours. The samples were classified according to melphalan resistance based on FMCA test results (Survival Index) from several hundred PHTC samples previously tested for melphalan. These data were used to establish cut-off lines to divide samples into three categories: Low, Intermediate or Extreme drug resistance (LDR, IDR and EDR, respectively) using the median value and median+1 standard deviation from that database. Melphalan and the new compounds J1, J3, and JV28 were subsequently classified into these groups. The classification of the melphalan resistance was performed according to the principles described by Larsson and Nygren, Anticancer Research 13; 1825–1830, 1993. The new peptides and P2 were tested at a concentration of 4 μM and melphalan at 10 μM. The results of the study is presented in Table 6 below.

TABLE 6

Circumvention of melphalan resistance

| | Number of samples (%) | | | |
|---|---|---|---|---|
| | LDR | IDR | EDR | Total |
| Melphalan | 8 (30%) | 10 (37%) | 9 (33%) | 27 |
| J1 | 13 (76%) | 3 (18%) | 1 (6%) | 17 |
| J3 | 23 (85%) | 4 (15%) | 0 (0%) | 27 |
| JV28 | 14 (82%) | 2 (12%) | 1 (6%) | 17 |
| P2 | 14 (74%) | 4 (21%) | 1 (5%) | 19 |

The results show that significantly fewer samples of the new peptides were classified as IDR and EDR indicating that these drugs have the ability to circumvent melphalan resistance. In this analysis it is assumed that at least half of the melphalan concentration may be reached in the clinical setting with the new peptides.

Test 7. Comparing the Activity of J1 and AcJ1

In order to investigate the difference in activity between a compound having a free amino group at the N-terminus and the same compound having said amino group protected, the acetylated form of J1 was synthesised and the activity compared with J1 using the FMCA procedure described above on the U-937 and RPMI 8226S cell lines. The results showed a several-fold lower potency (higher IC50; 0.61 and 2.9 μM respectively) for the acetylated form compared to J1 having a free amine, indicating a preference for the latter form with respect to antitumour activity.

Conclusions

The overall results demonstrate a significantly higher activity of the new compounds constituting the invention compared to all reference compounds (melphalan, sarcolysin and P2). Furthermore the novel compounds also demonstrated a broader spectrum of tumour type specific activity compared to the reference compounds with documented activity observed for many solid tumour diagnoses. Since these compounds also show a similar or slightly better relative activity in malignant vs normal cells, judged by taking the ratio of IC50s obtained in malignant (chronic lymphocytic leukemias) over normal lymphocytes, the clinical potential of these new compounds must be considered to be high.

What is claimed is:

1. A di- or tripepetide having the formula I:

(I)

wherein $R_1$ is alkyloxy, cycloalkyloxy, aryloxy, arylalkyloxy, $NH_2$, alkylamino, cycloalkylamino, or arylamino; $R_2$ is (IV)

wherein $R_3$ is independently $NH_2$, OH, O-alkyl, N-alkyl, O-acyl, NH-acyl, $N(CH_2CH_2Cl)_2$, $NO_2$, F, $CF_3$ or H, and n is 1 or 2; X is (II)

wherein $R_5$ is H; $R_4$ is a natural or modified cyclic or aromatic amino acid, or H; and pharmaceutically acceptable salts thereof.

2. A di- or tripepetide having the formula V:

(V)

wherein $R_1$ is alkyloxy, cycloalkyloxy, aryloxy, arylalkyloxy, $NH_2$, alkylamino, cycloalkylamino, or arylamino; $R_3$ is $NH_2$, OH, O-alkyl, N-alkyl, O-acyl, NH-acyl, $N(CH_2CH_2Cl)_2$, $NO_2$, F, $CF_3$ or H: and $R_4$ is a natural or modified cyclic or aromatic amino acid, or H; and pharmaceutically acceptable salts thereof.

3. A method of manufacturing a medicament, comprising:
formulating the peptide according to claim 1 with a pharmaceutically acceptable excipient.

4. The peptide according to claim 1, wherein $R_3$ is F.

5. The peptide according to claim 2, wherein $R_1$ is alkyloxy; $R_3$ is F, $CF_3$, H, OH, O-alkyl, $NO_2$, $N(CH_2CH_2Cl)_2$, NH-acyl or $NH_2$; and $R_4$ is H.

6. The peptide according to claim 5, which is L-melphanyl-p-L-fluoro-phenylalanine ethyl ester or a pharmaceutically acceptable salt thereof.

7. The peptide according to claim 5, which is L-melphanyl-p-L-fluoro-phenylalanine isopropyl ester or a pharmaceutically acceptable salt thereof.

8. The peptide according to claim 2, wherein $R_1$ is alkyloxy; $R_3$ is F, $CF_3$, H, OH, O-alkyl, NH-acyl, $NO_2$, $N(CH_2CH_2Cl)_2$ or $NH_2$; and $R_4$ is a natural or modified cyclic or aromatic amino acid.

9. The peptide according to claim 8, which is L-prolin-L-melphanyl-p-fluorophenylalanine ethyl ester or a pharmaceutically acceptable salt thereof.

10. A pharmaceutical composition for the treatment of malignant tumours, comprising at least one peptide compound according to claim 1, together with at least one pharmaceutically acceptable carrier and/or excipient.

11. The pharmaceutical composition according to claim 10, for the treatment of breast cancer, lung cancer, ovarian cancer, leukemias, lymphomas and multiple myeloma.

12. A method of treating malignant tumours, comprising:
administering a pharmaceutically effective dose of the peptide according to claim 1 to a subject in need thereof.

13. A method of manufacturing a medicament, comprising:
formulating the peptide according to claim 2 with a pharmaceutically acceptable excipient.

14. The peptide according to claim 2, wherein $R_3$ is F.

15. A pharmaceutical composition for the treatment of malignant tumors, comprising at least peptide compound according to claim 2, together with at least one pharmaceutically acceptable carrier and/or excipient.

16. The pharmaceutical composition according to claim 15, for the treatment of breast cancer, lung cancer, ovarian cancer, leukemias, lymphomas and multiple myeloma.

17. A method of treating malignant tumours, comprising:
administering a pharmaceutically effective dose of the peptide according to claim 2 to a subject in need thereof.

* * * * *

UNITED STATES PATENT AND TRADEMARK OFFICE
CERTIFICATE OF CORRECTION

PATENT NO. : 6,992,207 B2  
DATED : January 31, 2006  
INVENTOR(S) : Lewensohn et al.

Page 1 of 1

It is certified that error appears in the above-identified patent and that said Letters Patent is hereby corrected as shown below:

<u>Title page,</u>
Item [75], Inventors, should read -- Rolf Lewensohn, Danderyd (SE); Joakim Gullbo, Uppsala (SE); Rolf Larsson, Uppsala (SE); Hans Ehrsson, Bromma (SE); Kristina Luthman, Goteborg (SE) --.

Signed and Sealed this

Twenty-eighth Day of March, 2006

JON W. DUDAS
*Director of the United States Patent and Trademark Office*